(12) United States Patent
Shi et al.

(10) Patent No.: US 9,040,698 B2
(45) Date of Patent: May 26, 2015

(54) METHOD FOR PREPARING OPTICALLY PURE (+)-AMBRISENTAN AND (+)-DARUSENTAN

(75) Inventors: Yian Shi, Beijing (CN); Xianyou Peng, Beijing (CN); Peijun Li, Beijing (CN)

(73) Assignee: Institute of Chemistry Chinese Academy of Sciences, Beijing (CN)

( * ) Notice: Subject to any disclaimer, the term of this patent is extended or adjusted under 35 U.S.C. 154(b) by 0 days.

(21) Appl. No.: 14/125,054

(22) PCT Filed: Jul. 1, 2011

(86) PCT No.: PCT/CN2011/001095
§ 371 (c)(1),
(2), (4) Date: May 20, 2014

(87) PCT Pub. No.: WO2012/167406
PCT Pub. Date: Dec. 13, 2012

(65) Prior Publication Data
US 2014/0249309 A1    Sep. 4, 2014

(30) Foreign Application Priority Data

Jun. 10, 2011 (CN) .......................... 2011 1 0155478

(51) Int. Cl.
*C07D 239/24* (2006.01)
*C07D 239/34* (2006.01)
*C07D 239/60* (2006.01)

(52) U.S. Cl.
CPC ............ *C07D 239/34* (2013.01); *C07D 239/60* (2013.01)

(58) Field of Classification Search
CPC ...................................................... C07D 239/24
USPC ......................................... 544/298, 302, 318
See application file for complete search history.

(56) References Cited

U.S. PATENT DOCUMENTS 5,932,730 A    8/1999  Riechers et al.
8,404,840 B2 *  3/2013  Reddy et al. .................. 544/302

FOREIGN PATENT DOCUMENTS

| CN | 1160396 A | 9/1997 |
| CN | 102276536 A | 12/2011 |
| WO | 03066614 A1 | 8/2003 |
| WO | 2009017777 A2 | 2/2009 |
| WO | 2010070658 A2 | 6/2010 |
| WO | 2011004402 A2 | 1/2011 |

OTHER PUBLICATIONS

Wang et al., "A Diacetate Ketone-Catalyzed Asymmetric Epoxidation of Olefins", Journal of Organic Chemistry, vol. 74, No. 10, Apr. 23, 2009, pp. 3986-3989.
ISA Intellectual Property Office of China, International Search Report of PCT/CN2011/001095, WIPO, Mar. 22, 2012, 10 pages.

* cited by examiner

*Primary Examiner* — Golam M M Shameem
(74) *Attorney, Agent, or Firm* — Alleman Hall McCoy Russell & Tuttle LLP

(57) ABSTRACT

Disclosed is a method for preparing optically pure (+)-ambrisentan and (+)-darusentan, comprising: firstly catalyzing the asymmetric epoxidation of a β-unsaturated alkene using a chiral ketone derived from fructose or a hydrate thereof as a catalyst, and then subjecting the product to an epoxy compound ring-opening reaction and substitution reaction successively to obtain optically pure (+)-ambrisentan and (+)-darusentan.

9 Claims, No Drawings

METHOD FOR PREPARING OPTICALLY PURE (+)-AMBRISENTAN AND (+)-DARUSENTAN

CROSS-REFERENCE TO RELATED APPLICATIONS

This is the U.S. National Phase of International PCT Application Serial No. PCT/CN2011/001095, entitled "Method for Preparing Optically Pure (+)-Ambrisentan and (+)-Darusentan," filed on Jul. 1, 2011, which claims priority to Chinese Utility Model Application No. 201110155478.8, filed Jun. 10, 2011, both of which are hereby incorporated by reference in their entirety for all purposes.

TECHNICAL FIELD

The present invention relates to a method for preparing optically pure (+)-ambrisentan and (+)-darusentan.

BACKGROUND ART

Ambrisentan and darusentan were reported firstly in *J. Med. Chem.* 1996, 39, 2123-2128, as a selective antagonist for endothelin receptor A. Since then, their pharmacological properties have been further researched, as published in *J. Med. Chem.* 1996, 39, 2123-2128, U.S. Pat. No. 5,932,730, and WO 2009/017777 A2. As represented in formula (I), when R is methyl, its English name is (+)-ambrisentan, and its English nomenclature is (S)-2-(4,6-dimethylpyrimidin-2-yloxy)-3-methoxy-3,3-diphenylpropanoic acid; when R is methoxy, its English name is (+)-darusentan, and its English nomenclature is: (S)-2-(4,6-dimethoxypyrimidin-2-yloxy)-3-methoxy-3,3-diphenylpropanoic acid. Now, the ambrisentan has been approved by FDA in the United states under the trade name of Letairis to administrate orally for treating pulmonary hypertension. Darusentan may become a new drug for resistant hypertension.

The existing synthesis technique of ambrisentan or darusentan includes the Darzens reaction of benzophenone and methyl chloroacetate to produce a racemic epoxy compound, and ring opening the racemic epoxy compound under catalysis of boron trifluoride ether solution to obtain a prochiral alcohol, and further substitution reaction and hydrolysis reaction to obtain ambrisentan or darusentan. The existing method for obtaining optically pure (+)-ambrisentan or (+)-darusentan mainly relies on a resolving technique. For example, the prochiral alcohol is resolved by L-proline methyl ester or R-phenethylamine, see WO 2010/070658 A2 and WO 2011/004402 A2. It is well known that resolving of chiral drug has lower availability for materials, causing cost increase, and limiting the industrialized application of the product.

SUMMARY

The aim of the present invention is to provide a method for preparing optically pure (+)-ambrisentan and (+)-darusentan.

The method for preparing the compound represented by formula (I) provided in the present invention includes the following steps:

(1) in the presence of a catalyst and an oxidant, conducting an epoxidation reaction of 3,3-diphenyl acrylate represented by formula (II) to obtain (2S)-epoxy-3,3-diphenyl acrylate represented by formula (III); the catalyst is chiral ketone derived from fructose represented by formula (IV) or a hydrate thereof represented by formula (V);

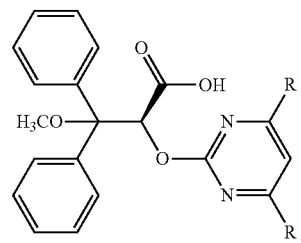
(I)

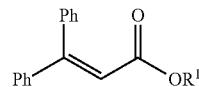
(II)

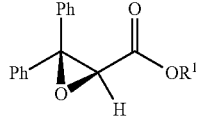
(III)

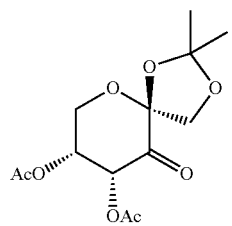
(IV)

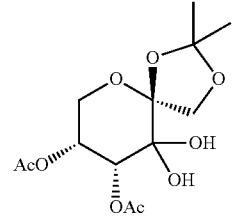
(V)

wherein, Ph is phenyl; Ac is acetyl; $R^1$ is selected from any one of methyl, ethyl, n-propyl, isopropyl, n-butyl, tert-butyl, cyclohexyl and benzyl; R is methyl or methoxy;

(2) in the presence of acidic catalyst and methanol, conducting an epoxidation reaction of (2S)-epoxy-3,3-diphenylacrylate represented by formula (III) to obtain (2S)-2-hydroxyl-3-methoxy-3,3-diphenylacrylate represented by formula (VI),

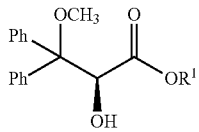
(VI)

wherein, Ph is phenyl; Ac is acetyl; $R^1$ is selected from any one of methyl, ethyl, n-propyl, isopropyl, n-butyl, tert-butyl, cyclohexyl and benzyl;

(3) in the presence of alkaline compound, conducting a nucleophilic substitution reaction of (2S)-2-hydroxyl-3-methoxy-3,3-diphenylacrylate represented by formula (VI) and methylsulfonyl pyrimidine represented by formula (VII) to obtain a compound represented by formula (VIII);

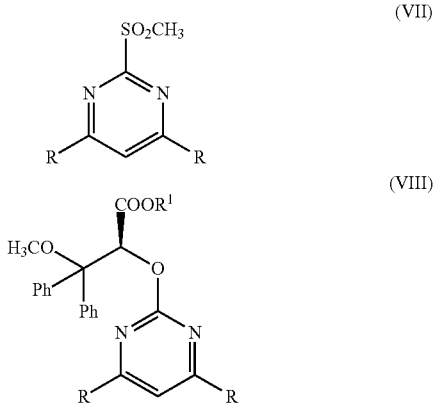

wherein, R is methyl or methoxy; $R^1$ is selected from any one of methyl, ethyl, n-propyl, isopropyl, n-butyl, tert-butyl, cyclohexyl and benzyl;

(4) in the presence of alkaline compound, after the compound represented by formula (-VIII) subjected to a hydrolysis reaction, and is acidized by protonic acid to obtain the compound represented by formula (I).

In the above preparation process, the oxidant in step (1) can be selected from any one of sodium perbromate, sodium periodate, potassium monopersulfate, potassium peroxymonosulfate and hydrogen peroxide.

In the above preparation process, the molar ratio of 3,3-diphenyl acrylate represented by formula (II) in step (1), the oxidant and the catalyst can be 1:(2.5-10):(0.10-1.0), particularly 1:5:0.9 or 1:5.6:0.34; the temperature of said epoxidation reaction can be −15° C.-50° C., particularly −5° C.-5° C.; and the time for said epoxidation reaction can be 5 hours-24 hours, particularly 5 hours.

In the above preparation process, said acidic catalyst in step (2) can be protonic acid or Lewis acid; said protonic acid can be selected from any one of hydrochloric acid, sulphuric acid, paratoluenesulfonic acid, benzene sulfonic acid and camphorsulfonic acid; said Lewis acid can be selected from any one of boron trifluoride ether, boron trifluoride methanol, tin bichloride, tetraisopropoxy titanium and titanium tetrachloride; the molar ratio of (2S)-epoxy-3,3-diphenyl acrylate represented by formula (III) and said acidic catalyst can be 1:0.01-1.0, particularly 1:0.013.

In the above preparation process, the temperature of said epoxidation ring-opening reaction in step (2) can be −15° C.-50° C., particularly 0° C. or 20° C., the time for said epoxidation ring-opening reaction can be 5 hours-24 hours, particularly 8 hours.

In the above preparation process, said alkaline compound in step (3) and step (4) can be selected from any one of metal hydride, metal carbonate, metal bicarbonate, metal hydroxide, metal aminate and metal alkoxide; said metal hydride can be lithium hydride, sodium hydride or potassium hydride; said metal carbonate can be sodium carbonate, potassium carbonate or cesium carbonate; said metal bicarbonate can be sodium bicarbonate or potassium bicarbonate; said metal hydroxide can be lithium hydroxide, sodium hydroxide, potassium hydroxide or barium hydroxide; said metal aminate can be lithium aminate, sodium aminate or potassium aminate; said metal alkoxide can be sodium methoxide, sodium ethoxide, sodium isopropoxide or sodium tert-butoxide.

In the above preparation process, in step (3), the molar ratio of (2S)-2-hydroxyl-3-methoxy-3,3-diphenylacrylate represented by formula (VI), methylsulfonyl pyrimidine represented by formula (VII) and said alkaline compound can be 1:(1.1-1.2):(0.5-0.6), particularly 1:1.2:0.6; the temperature of said nucleophilic substitution reaction can be 20° C.-90° C., particularly 80° C. or 90° C., the time for said nucleophilic substitution reaction can be 0.5 hours-3 hours, particularly 3 hours.

In the above preparation process, in step (4), the molar ratio of the compound represented by formula (-VIII) and said alkaline compound can be 1:(2-5), particularly 1:5; the temperature of said hydrolysis reaction can be 20° C.-90° C., particularly 80° C., the time for said hydrolysis reaction can be 8 hours; said protonic acid can be selected from any one of hydrochloric acid, sulphuric acid, paratoluene sulfonic acid, benzene sulfonic acid and camphorsulfonic acid.

In the above preparation process, step (1) can further include the step of adding an additive; said additive can be at least one of a phase transfer catalyst, disodium ethylene diamine tetraacetate aqueous solution and said alkaline compound; said phase transfer catalyst can be selected from any one of benzyl triethyl ammonium chloride, tetrabutyl ammonium bromide, tetrabutyl ammonium chloride, tetrabutyl ammonium iodide, tetrabutyl ammonium bisulfate, trioctylmethyl ammonium chloride, dodecyltrimethyl ammonium chloride and tetradecyl trimethyl ammonium chloride; the molar concentration of said disodium ethylene diamine tetraacetate aqueous solution can be 0-0.001 mol/L, but can not be 0; the molar ratio of said phase transfer catalyst and 3,3-diphenyl acrylate represented by formula (II) can be 1:(0.03-1), particularly 1:0.06; the volume ratio of said disodium ethylene diamine tetraacetate aqueous solution and a solvent of said epoxidation reaction can be 1:(1-2), particularly 1:2; the molar ratio of said alkaline compound and 3,3-diphenyl acrylate represented by formula (II) can be 1:(0.05-20), particularly 1:15.

In the above preparation process, after said hydrolysis reaction, step (4) further includes the step of extracting with ether solvent and/or $C_5$-$C_{10}$ paraffins solvent, removing possible organic impurity; after said acidification, further includes the step of extracting with ester solvent, the racemic ambrisentanin in this extracting process can automatically congregate into insoluble solid, filtering out the racemic ambrisentan, concentrating said ester solvent, then obtaining optically pure (+)-ambrisentan; said ether solvent can be ether, dipropyl ether, dibutyl ether, methyl tertiary butyl ether, 1,3-dioxane, 1,4-dioxane, tetrahydrofuran, dimethoxymethane, ethylene glycol monomethyl ether, glycol dimethyl ether, ethylene glycol monomethyl ether, ethylene glycol diethyl ether or tert-butyl methylether; said $C_5$-$C_{10}$ paraffins solvent can be pentane, n-hexane, n-heptane, toluene or xylene; said amide solvent can be N, N-dimethyl methanamide or N, N-dimethyl acetamide; said ester solvent can be ethyl acetate, methyl acetate, propyl acetate, tert-butyl acetate or ethyl formate.

In the above preparation process, said medium in the reactions of step (1), step (2), step (3) and step (4) can be selected from at least one of ether solvent, alcohol solvent, ester solvent, halogenated alkane solvent, $C_5$-$C_{10}$ paraffins solvent, amide solvent, nitrile solvent and water; said ether solvent can be ether, dipropyl ether, dibutyl ether, methyl tertiary butyl ether, 1,3-dioxane, 1,4-dioxane, tetrahydrofuran, dimethoxy methane, ethylene glycol monomethyl ether, glycol dimethyl ether, ethylene glycol monomethyl ether, ethylene glycol diethyl ether or tert-butyl methylether; said alcohol solvent can be methanol, ethanol, normal propyl alcohol, isopropanol, normal butanol, sec-butyl alcohol, tert-butyl alcohol or glycol; said ester solvent can be ethyl acetate, methyl acetate, propyl acetate, tert-butyl acetate or ethyl formate; said halogenated alkane solvent can be methylene dichloride, trichloromethane or 1,2-methylene dichloride; said $C_5$-$C_{10}$ paraffins solvent can be pentane, n-hexane, n-heptane, toluene or xylene; said amide solvent can be N,N-dimethyl methanamide or N,N-dimethyl acetamide; said nitrile solvent can be acetonitrile or propionitrile.

DETAILED DESCRIPTION

The experimental methods used in the following examples are the conventional methods, unless otherwise indicated.

The present invention will be readily understood by the following examples, but these examples are used to illustrate the present invention, and not to limit the scope of the invention.

The materials, reagents etc. used in the following examples all can be obtained commercially, unless otherwise indicated.

The molecular formula of potassium peroxymonosulfate used in the following examples of the present invention is 2 $KHSO_5 \cdot KHSO_4 \cdot K_2SO_4$, which is purchased from Bei Jing OuHe technology Co., Ltd, under trade name of Oxone®.

EXAMPLE 1

Preparation of (+)-ambrisentan((2S)-2-(4,6-dimethylpyrimidin-2-yloxy)-3-methoxy-3,3-diphenylpropanoic acid)

(1) Preparation of (2S)-3,3-diphenyl-2,3-ethyl epoxy propionate

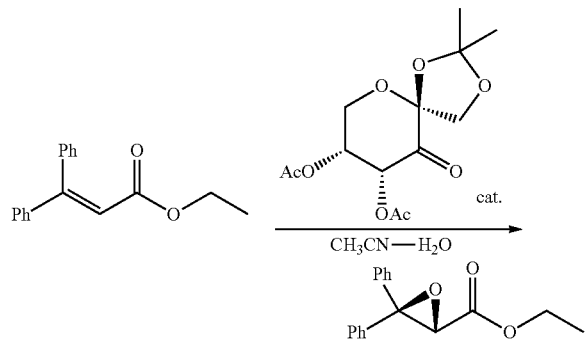

The reaction equation is shown by above equation, wherein Ph is phenyl; Ac is acetyl;

To 50 L reactor with the mechanical agitator, 3,3-diphenyl ethyl acrylate (0.536 mol, 135.0 g) dissolved in 3.0 L acetonitrile, and 0.12 M of chiral ketone derived from fructose represented by formula (IV) dissolved in 1.5 L acetonitrile were added, and tetra-n-butylammonium bisulfate (36 mmol, 12.2 g) was then added, then the aqueous solution containing 3.0 L $1 \times 10^{-4}$M of disodium ethylene diamine tetraacetate was added; the coolant was passed into the jacket of the reactor, and the temperature of the reactor was adjusted to −5° C.-+5° C.; the mixture of 1.85 kg potassium peroxymonosulfate (Oxone®) and 0.78 kg $NaHCO_3$ (9.29 mol) crushed by Chinese medicine mill was added in portions under stirring for about 4.5 hours, thereafter, the reaction mixture was continued at this condition to be stirred (in this system, the molar ratio of 3,3-diphenyl ethyl acrylate, potassium peroxymonosulfate and chiral ketone derived from fructose represented by formula (IV) is 1:5:0.34), and the reaction was detected using gas chromatograph at timing; the reaction completed after 5 hours, and 5.0 L water was added to dilute the reaction liquid, then extracting with 5.0 L ethyl acetate; 2.5 L ethyl acetate was further added into the water phase to extract; the organic phases were combined, and concentrated to remove the solvent, thereby obtaining 162.56 g (2S)-3,3-diphenyl-2,3-ethyl epoxy propionate, the crude product has yield greater than 99%, and was used in the next step reaction without purification, the nuclear magnetic conversion rate is 92%, the enantiomer was detected using high performance liquid chromatography to excess 86.9%. The analysis condition: the column model is Chiralcel OD-H, the volume ratio of n-hexane and isopropanol is 98:2, the analysis wavelength is 210 nm, the flow velocity of the mobile phase is 1 mL/min, $t_1$=9.5 min, $t_2$=13.01 min, 86.9% ee.

IR (film) 1760, 1731 $cm^{-1}$; $^1$H NMR [400 MHz, $CDCl_3$] δ 7.46-7.44 (m, 2H), 7.36-7.31 (m, 8H), 3.99 (m, 3H), 0.96 (t, J=7.2 Hz, 3H); $^{13}$C NMR [100 MHz, $CDCl_3$] δ 166.99, 138.98, 135.62, 128.67, 128.53, 128.36, 128.13, 127.04, 66.57, 62.16, 61.43, 13.96.

(2) Preparation of (2S)-2-hydroxyl-3-methoxy-3,3-diphenyl ethyl propionate

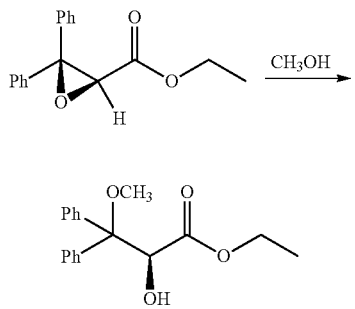

162.56 g unpurified (2S)-epoxy-3,3-diphenyl ethyl acrylate crude product compound obtained in step (1) was dissolved in 100 mL methanol, 1 mL boron trifluoride ether (the molar ratio of (2S)-epoxy-3,3-diphenylethyl acrylate and boron trifluoride ether is 1:0.013) was added to conduct the epoxidation ring-opening reaction; the reaction temperature was controlled at 20° C., after the reaction of 8 hours, concentrating the reaction liquid, extracting the reaction liquid with ethyl acetate and water, after concentrating ethyl acetate, 166.0 g intermediate (2S)-2-hydroxyl-3-methoxy-3,3-diphenylethyl propionate was obtained, the crude product yield is 92%, the enantiomer was detected using high performance liquid chromatography to excess 86.9%. The analysis condition: column model is Chiralcel OD-H, the volume ratio of n-hexane and isopropanol was 98:2, the analysis wavelength is 210 nm, the flow velocity of the mobile phase is 1 mL/min, $t_1$=9.71 min, $t_2$=14.51 min, 85.8% ee.;

IR (film) 1769, 1758 $cm^{-1}$; $^1$H NMR [400 MHz, $CDCl_3$] δ 7.50-7.28 (m, 10H), 5.18 (s, 1H), 4.10 (t, 2H), 3.20 (s, J=7.2 Hz, 3H), 3.03 (s, 1H), 1.17 (t, J=7.2 Hz, 3H); $^{13}$C NMR [100 MHz, $CDCl_3$] δ 172.48, 141.13, 140.32, 128.97, 128.73, 128.99, 127.81, 127.76, 127.62, 85.01, 77.42, 61.76, 52.62, 14.07.

(3) Preparation of (2S)-2-(4,6-dimethylpyrimidin-2-yloxy)-3-methoxy-3,3-diphenyl ethyl propionate

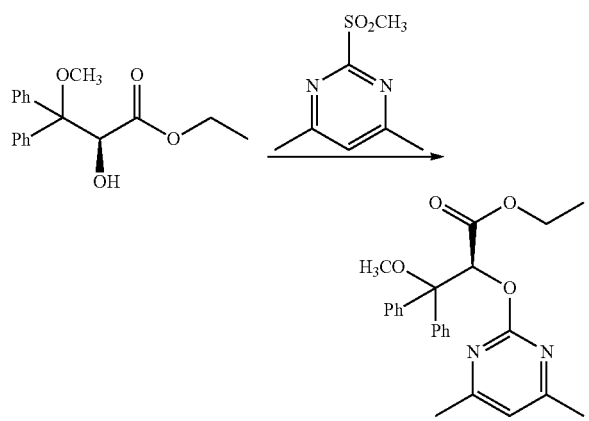

To 166.0 g intermediate (2S)-2-hydroxyl-3-methoxy-3,3-diphenyl ethyl propionate obtained in step (2), 750 mL of N,N-dimethyl methanamide and 45.54 g of potassium carbonate were added, after stirring for half an hour, 4,6-dimethyl-2-methylsulfonyl pyrimidine was added to conduct the nucleophilic substitution reaction in 80° C. oil bath, in this system, the molar ratio of (2S)-2-hydroxyl-3-methoxy-3,3-diphenylethyl propionate, 4,6-dimethyl-2-methylsulfonyl pyrimidine and potassium carbonate is 1:1.2:0.6; after about 3 hours when monitoring the accomplishment of the material consumption using the nuclear magnetism, ethyl acetate and water were added to extract the reaction liquid, the ethyl acetate layer was concentrated to obtain 237.70 g intermediate (2S)-2-(4,6-dimethylpyrimidin-2-yloxy)-3-methoxy-3,3-diphenyl ethyl propionate, the crude product yield is greater than 99%, the enantiomer was detected using high performance liquid chromatography to excess 85.9%. The analysis condition: column model is Chiralcel OD-H, the volume ratio of n-hexane and isopropanol is 98:2, the analysis wavelength is 210 nm, the flow velocity of the mobile phase is 1 mL/min, $t_1$=10.15 min, $t_2$=11.87 min, 85.9% ee.

IR (film) 1750 cm$^{-1}$; $^1$H NMR [400 MHz, CDCl$_3$] δ 7.45 (d, J=7.2 Hz, 2H), 7.39 (d, J=7.2 Hz, 2H), 7.33-7.19 (m, 7H), 6.70 (s, 1H), 6.12 (s, 1H), 4.01-3.85 (m, 2H), 3.50 (s, 3H) 2.38 (s, 6H), 0.93 (t, J=6.8 Hz, 3H); $^{13}$C NMR [100 MHz, CDCl$_3$] δ 169.51, 168.70, 163.86, 142.50, 141.29, 128.54, 128.03, 127.97, 127.94, 127.47, 127.40, 115.03, 83.76, 79.23, 77.43, 60.66, 53.92, 23.99, 13.93; Anal. Calcd For C$_{24}$H$_{26}$N$_2$O$_4$: C, 70.92; H, 6.45; N, 6.89. Found: C, 70.72; H, 6.47; N, 6.83.

(4) Preparation of (2S)-2-(4,6-dimethylpyrimidin-2-yloxy)-3-methoxy-3,3-diphenylpropanoic acid ((+)-ambrisentan)

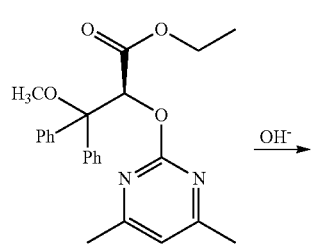

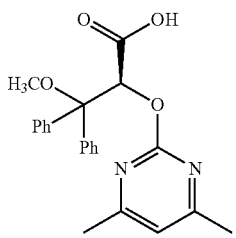

237.7 g intermediate (2S)-2-(4,6-dimethylpyrimidin-2-yloxy)-3-methoxy-3,3-diphenyl ethyl propionate obtained in step (3) was dissolved in 1.2 L organic solvent 1,4-dioxane, 600 mL aqueous solution containing 92.3 g sodium hydroxide was added (wherein, the molar ratio of (2S)-2-(4,6-dimethylpyrimidin-2-yloxy)-3-methoxy-3,3-diphenyl ethyl propionate and sodium hydroxide is 1:4), the reaction temperature is 80° C., after the reaction of 8 hours, the reaction liquid was concentrated, and extracted with (1 L, 0.5 L, 0.5 L) ether to remove organic impurity, hydrochloric acid was added into the extracted water phase to adjust to pH 3, at this time a great deal of solid appeared; then, 1.0 L ethyl acetate was added into the water phase, the insoluble matter were filtered and removed (after analysis, these insoluble matter was found to be racemic ambrisentan, 23.37 g), the organic layer was concentrated, thereby obtaining 103.9 g optically pure (+)-ambrisentan. From 3,3-diphenylethyl acrylate to the optically pure (+)-ambrisentan, the yield is 52.3%. Take a little amount of the obtained ambrisentan to react with diazomethane, and obtain (2S)-2-(4,6-dimethylpyrimidin-2-yloxy)-3-methoxy-3,3-diphenyl methyl propionate, and the enantiomer of ambrisentan was detected to be excess. (2S)-2-(4,6-dimethylpyrimidin-2-yloxy)-3-methoxy-3,3-diphenyl ethyl propionate: detecting using high efficiency liquid chromatography, and the enantiomer excessed 99.1%. The analysis condition: column model is Chiralcel OD-H, the volume ratio of n-hexane and isopropanol is 98:2, the analysis wavelength is 210 nm, the flow velocity of the mobile phase is 1 mL/min, $t_1$=11.61 min, $t_2$=14.05 min, 99.1% ee.

$[α]_D^{25}$=+174.2 (c=0.5, MeOH); m.p.>150° C. yellow, >180° C. black, 182° C. melt; $^1$H NMR [400 MHz, CDCl$_3$] δ 7.43 (d, J=Hz, 2H), 7.29-7.19 (m, 8H), 6.63 (s, 1H), 6.30 (s, 1H), 3.26 (s, 3H) 2.31 (s, 6H); $^{13}$C NMR [100 MHz, CDCl$_3$] δ 178.98, 170.54, 169.70, 163.48, 139.91, 138.91, 128.77, 128.67, 128.22, 128.08, 115.34, 84.67, 77.55, 53.49, 23.93; $^1$H NMR [400 MHz, DMSO] δ 12.53 (s, 1H), 7.34-7.20 (m, 10H), 6.95 (s, 1H), 6.14 (s, 1H), 3.37 (s, 3H) 2.34 (s, 6H); $^{13}$C NMR [100 MHz, DMSO] δ 169.01, 163.14, 142.59, 141.41, 127.80, 127.68, 127.64, 127.19, 126.95, 114.72, 83.12, 77.55, 52.99, 23.30.

EXAMPLE 2

Preparation of (+)-darusentan ((2S)-2-(4,6-dimethoxypyrimidin-2-yloxy)-3-methoxy-3,3-diphenylpropanoic acid)

(1) Preparation of (2S)-3,3-diphenyl-2,3-epoxyethyl propionate

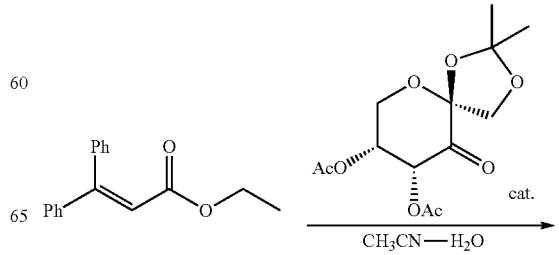

-continued

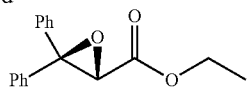

The reaction equation is represented by the above equation, wherein Ph is phenyl; Ac is acetyl;

To 50 L reactor with the mechanical agitator, 3,3-diphenyl ethyl acrylate (0.267 mol, 67.3 g) dissolved in 1.5 L acetonitrile, and 0.12 M chiral ketone derived from fructose represented by formula (IV) dissolved in 0.75 L acetonitrile were added, and tert-n-butylammonium bisulfate (18 mmol, 6.1 g) was added, then aqueous solution containing 1.5 L $1\times10^{-4}$ M disodium ethylene diamine tetraacetate added; a coolant was passed into the jacket of the reactor, the temperature within the reactor was adjusted to −5° C.-+5° C.; the mixture of 0.923 kg (1.5 mol) potassium peroxymonosulfate (Oxone®) and 0.391 kg $NaHCO_3$ (4.65 mol) crushed by Chinese medicine mill was added in portions under stirring for about 4.5 hours, after that, the reaction mixture was continued at this condition to be stirred (in this system, the molar ratio of 3,3-diphenyl ethyl acrylate, potassium peroxymonosulfate and chiral ketone derived from fructose represented by formula (IV) is 1:5.6:0.34), and the reaction was detected in timing using gas chromatograph; the reaction completes after 5 hours, and 2.0 L water was added to dilute the reaction liquid, then extracting with 3.0 L ethyl acetate; 0.5 L ethyl acetate was further added into the water phase to extract; the organic phases were combined, and concentrated to remove the solvent, thereby obtaining 78.84 g (2S)-3,3-diphenyl-2,3-ethyl epoxy propionate with crude product yield of greater than 99%, and was used in the next reaction without purification. The nuclear magnetic conversion rate is 92%, the enantiomer was detected using high performance liquid chromatography to excess 86.9%. The analysis condition: column model is Chiralcel OD-H, the volume ratio of n-hexane and isopropanol is 98:2, the analysis wavelength is 210 nm, the flow velocity of the mobile phase is 1 mL/min, $t_1$=9.5 min, $t_2$=13.01 min, 86.9% ee.

IR (film) 1760 $cm^{-1}$, 1731 $cm^{-1}$; $^1H$ NMR [400 MHz, $CDCl_3$] δ 7.46-7.44 (m, 2H), 7.36-7.31 (m, 8H), 3.99 (m, 3H), 0.96 (t, J=7.2 Hz, 3H); $^{13}C$ NMR [100 MHz, $CDCl_3$] δ 166.99, 138.98, 135.62, 128.67, 128.53, 128.36, 128.13, 127.04, 66.57, 62.16, 61.43, 13.96.

(2) Preparation of (2S)-2-hydroxyl-3-methoxy-3,3-diphenylethyl propionate

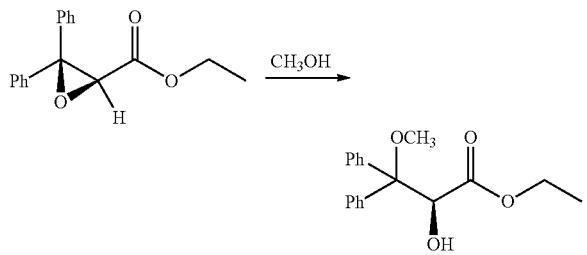

77.12 g unpurified (2S)-epoxy-3,3-diphenylethyl acrylate crude product compound obtained in step (1) was dissolved in 75 mL methanol, 0.5 mL boron trifluoride ether (the molar ratio of (2S)-epoxy-3,3-diphenylethyl acrylate and boron trifluoride ether is 1:0.013) was added to conduct the ring-opening; the reaction temperature was controlled at 0° C., after the reaction of 8 hours, concentrating the reaction liquid, extracting the reaction liquid with ethyl acetate and water, after concentrating ethyl acetate, 77.63 g intermediate (2S)-2-hydroxyl-3-methoxy-3,3-diphenylethyl propionate was obtained with crude product yield of 86%, the enantiomer was detected using high efficiency liquid chromatography to excess 86%. The analysis condition: column model is Chiralcel OD-H, the volume ratio of n-hexane and isopropanol is 98:2, the analysis wavelength is 210 nm, the flow velocity of the mobile phase is 1 mL/min, $t_1$=9.71 min, $t_2$=14.51 min, 86% ee.;

IR (film) 1769 $cm^{-1}$, 1758 $cm^{-1}$; $^1H$ NMR [400 MHz, $CDCl_3$] δ 7.50-7.28 (m, 10H), 5.18 (s, 1H), 4.10 (t, 2H), 3.20 (s, J=7.2 Hz, 3H), 3.03 (s, 1H), 1.17 (t, J=7.2 Hz, 3H); $^{13}C$ NMR [100 MHz, $CDCl_3$] δ 172.48, 141.13, 140.32, 128.97, 128.73, 128.99, 127.81, 127.76, 127.62, 85.01, 77.42, 61.76, 52.62, 14.07.

(3) Preparation of (2S)-2-[(4,6-dimethoxypyrimidin-2-yloxy)-3-methoxy-3,3-diphenyl ethyl propionate

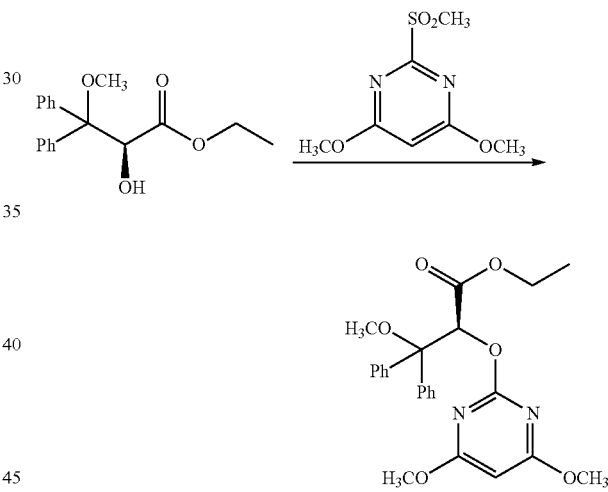

To 2.4 g intermediate (2S)-2-hydroxyl-3-methoxy-3,3-diphenylethyl propionate obtained in step (2), 11 mL of N,N-dimethyl methanamide and 0.66 g of potassium carbonate were added, after stirring for half an hour, 4,6-dimethoxy-2-methylsulfonyl pyrimidine was added to conduct nucleophilic substitution reaction in 90° C. oil bath, wherein the molar ratio of (2S)-2-hydroxyl-3-methoxy-3,3-diphenylethyl propionate, 4,6-dimethoxy-2-methylsulfonyl pyrimidine and potassium carbonate is 1:1.2:0.6; after about 3 hours when monitoring the accomplishment of the material consumption using the nuclear magnetism, ethyl acetate and water were added to extract the reaction liquid, the ethyl acetate was concentrated to obtain 2.38 g intermediate (2S)-2-(4,6-dimethoxypyrimidin-2-yloxy)-3-methoxy-3,3-diphenyl-ethyl propionate with crude product yield of 68%. $^1H$ NMR [400 MHz, $CDCl_3$] δ 7.45 (d, J=8.0 Hz, 2H), 7.39-7.21 (m, 8H), 6.02 (s, 1H), 5.72 (s, 1H), 3.90 (q, J=7.2 Hz, 2H), 3.86 (s, 3H) 3.42 (s, 3H), 0.91 (t, J=7.2 Hz, 3H); $^{13}C$ NMR [100 MHz, CDCl$_3$] δ 172.93, 168.60, 163.36, 142.12, 141.12, 128.69, 128.24, 127.99, 127.88, 127.57, 84.40, 83.69, 79.31, 60.78, 54.39, 53.69.

(4) Preparation of (2S)-2-(4,6-dimethoxypyrimidin-2-yloxy)-3-methoxy-3,3-diphenylpropanoic acid ((+)-darusentan)

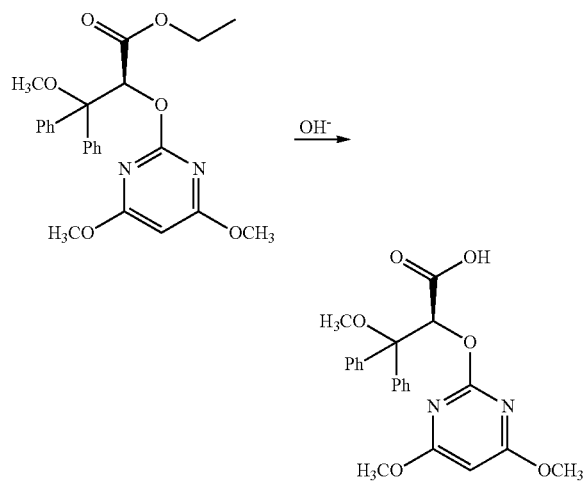

2.16 g intermediate (2S)-2-[(4,6-dimethoxypyrimidin-2-yloxy)-3-methoxy-3,3-diphenyl ethyl propionate obtained in step (3) was dissolved in 20 mL organic solvent 1,4-dioxane, 10 mL aqueous solution containing 0.99 g sodium hydroxide was added (wherein, the molar ratio of (2S)-2-[(4,6-dimethoxypyrimidin-2-yloxy)]-3-methoxy-3,3-diphenyl-ethyl propionate and sodium hydroxide is 1:5), the reaction temperature is 80° C., after the reaction of 8 hours, the reaction liquid was concentrated, and extracted with ether to remove organic impurity, hydrochloric acid was added into the extracted water phase to adjust pH to about 3; 100 mL ethyl acetate was added into the water phase, the organic layer was concentrated, obtaining 1.32 g optically pure white foam solid (+)-darusentan with yield of 65%. [a]$_D^{25}$=+91.4 (c=1.0, MeOH); $^1$H NMR [400 MHz, DMSO] δ 7.41-7.12 (m, 10H), 6.17 (s, 1H), 5.73 (s, 1H), 3.88 (s, 6H), 3.32 (s, 3H).

Take a little amount of the obtained darusentan to react with diazomethane, and obtain (2S)-2-(4,6-dimethoxypyrimidin-2-yloxy)-3-methoxy-3,3-diphenylmethyl propionate, and the enantiomer of darusentan was detected to be excess. (2S)-2-(4,6-dimethylpyrimidin-2-yloxy)-3-methoxy-3,3-diphenylmethyl propionate: detecting using high performance liquid chromatography and the enantiomer excessed 99.1%; the analysis condition: column model is Chiralcel OD-H, the volume ratio of n-hexane and isopropanol is 98:2, the analysis wavelength is 210 nm, the flow velocity of the mobile phase is 1 mL/min, t$_1$=7.16 min, t$_2$=8.55 min, 83.2% ee.

INDUSTRIAL APPLICABILITY

The preparation method provided by the present invention has the following advantages:

(1) the present invention uses the following step as the critical step: adopting the cheap chiral ketone derived from fructose represented by formula (IV) or a hydrate thereof represented by formula (V) as a catalyst to catalyze asymmetrical epoxidation of 3,3-diphenyl acrylate represented by formula (II), then by several derivations to obtain optically pure (+)-ambrisentan and (+)-darusentan. Commercial, non-toxic and environment friendly reagents are selected.

(2) the synthetic route of the present invention aims at achieving the industrial preparation of the optically pure (+)-ambrisentan and (+)-darusentan, and the industrially easily achieved processes such as extraction, filtration or recrystallization etc. are selected during post treatment to obtain target product.

(3) in the steps of purifying ambrisentan or darusentan, it is found that in step (4) of the present invention, when using the ester solvent to extract, racemic ambrisentan automatically congregates to precipitate out in solid, which are difficult to dissolve in water and ester solvent. The extracted ester solvent was concentrated, and then the optically pure (+)-ambrisentan or (+)-darusentanobtain can be obtained. HPLC shows that the excess of the enantiomer (e.e.) is greater than 98.8%, and can be greater than 99.1% preferably. The present invention uses asymmetrical synthesis method, reducing the content of another isomer, and increasing the yield of target compound.

The invention claimed is:

1. A method for preparing a compound represented by formula (I), including the steps:

(1) in the presence of a catalyst and an oxidant, conducting an epoxidation reaction of 3,3-diphenyl acrylate represented by formula (II) to obtain (2S)-epoxy-3,3-diphenyl acrylate represented by formula (III); said catalyst is a chiral ketone derived from fructose represented by formula (IV) or a hydrate thereof represented by formula (V), and characterized in that the oxidant is selected from any one of sodium perbromate, sodium periodate, potassium monopersulfate, potassium peroxymonosulfate and hydrogen peroxide,

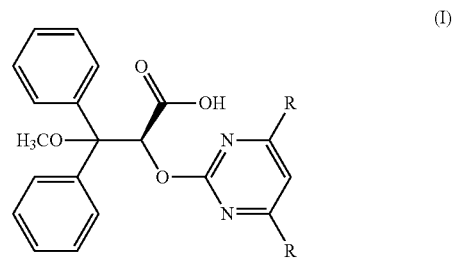

(I)

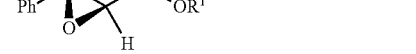

(II)

(III)

(IV)

-continued (V)

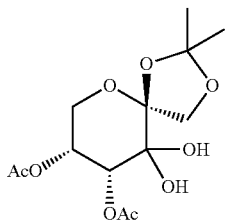

wherein, Ph is phenyl; Ac is acetyl; R1 is selected from any one of methyl, ethyl, n-propyl, isopropyl, n-butyl, tert-butyl, cyclohexyl and benzyl; R is one of methyl and methoxy;

(2) in the presence of an acidic catalyst and methanol, conducting an epoxy ring-opening reaction of (2S)-epoxy-3,3-diphenyl acrylate represented by formula (III) to obtain (2S)-2-hydroxyl-3-methoxy-3,3-diphenyl acrylate represented by formula (VI);

(VI)

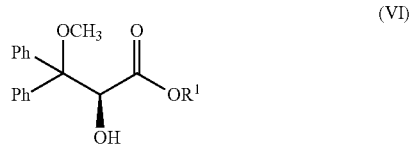

wherein, Ph is phenyl; Ac is acetyl; R1 is selected from any one of methyl, ethyl, n-propyl, isopropyl, n-butyl, tert-butyl, cyclohexyl and benzyl;

(3) in the presence of an alkaline compound, conducting a nucleophilic substitution reaction of (2S)-2-hydroxyl-3-methoxy-3,3-diphenylacrylate represented by formula (VI) and methylsulfonyl pyrimidine represented by formula (VII) to obtain a compound represented by formula (VIII);

(VII)

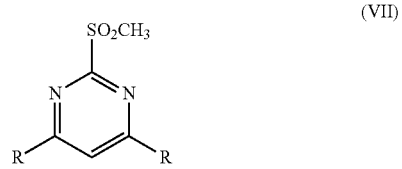

(VIII)

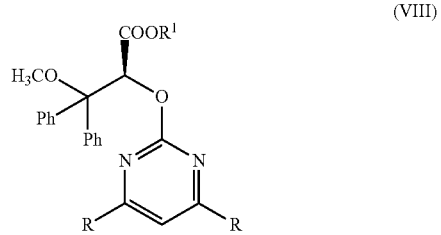

wherein, R is one of methyl and methoxy; R1 is selected from any one of methyl, ethyl, n-propyl, isopropyl, n-butyl, tert-butyl, cyclohexyl and benzyl;

(4) in the presence of an alkaline compound, conducting a hydrolysis reaction of the compound represented by formula (VIII), then acidifying by a protonic acid, thereby obtaining the compound represented by formula (I).

2. The method according to claim 1, characterized in that: the molar ratio of 3,3-diphenyl acrylate represented by formula (II), the oxidant and the catalyst in the step (1) is 1:(2.5-10):(0.10-1.0); the temperature of the epoxidation reaction is −15° C.-50° C.; the time for the epoxidation reaction is 5 hours-24 hours.

3. The method according to claim 2, characterized in that: the acidic catalyst in the step (2) is one of protonic acid and Lewis acid; the protonic acid is selected from any one of hydrochloric acid, sulphuric acid, paratoluenesulfonic acid, benzene sulfonic acid and camphorsulfonic acid; the Lewis acid is selected from any one of boron trifluoride ether solution, tin bichloride, tetraisopropoxy titanium and titanium tetrachloride; the molar ratio of (2S)-epoxy-3,3-diphenyl acrylate represented by formula (III) and the acidic catalyst is 1:(0.01-1).

4. The method according to claim 3, characterized in that: the temperature of the epoxy ring-opening reaction in the step (2) is −15° C.-50° C., and the time for the epoxy ring-opening reaction is 5 hours-24 hours.

5. The method according to claim 4, characterized in that: the alkaline compound in the steps (3) and (4) is selected from any one of metal hydride, metal carbonate, metal bicarbonate, metal hydroxide, metal aminate and metal alkoxide; the metal hydride is one of lithium hydride, sodium hydride and potassium hydride; the metal carbonate is one of sodium carbonate, potassium carbonate and cesium carbonate; the metal bicarbonate is one of sodium bicarbonate and potassium bicarbonate; the metal hydroxide is one of lithium hydroxide, sodium hydroxide, potassium hydroxide and barium hydroxide; the metal aminate is one of lithium aminate, sodium aminate and potassium aminate; the metal alkoxide is one of sodium methoxide, sodium ethoxide, sodium isopropoxide and sodium tert-butoxide.

6. The method according to claim 5, characterized in that: the molar ratio of (2S)-2-hydroxyl-3-methoxy-3,3-diphenyl acrylate represented by formula (VI), methylsulfonyl pyrimidine represented by formula (VII) and the alkaline compound in the step (3) is 1:(1.1-1.2):(0.5-0.6); the temperature of the nucleophilic substitution reaction is 20° C.-90° C., the time for the nucleophilic substitution reaction is 0.5 hours-3 hours.

7. The method according to claim 6, characterized in that: the molar ratio of the compound represented by formula (VIII) and the alkaline compound in the step (4) is 1:(2-5); the temperature of the hydrolysis reaction is 20° C.-90° C., and the time for the hydrolysis reaction is 1 hour-24 hours; the protonic acid is selected from any one of hydrochloric acid, sulphuric acid, paratoluenesulfonic acid, benzene sulfonic acid and camphorsulfonic acid; in the step (4), after the hydrolysis reaction, further including the step of extracting with ether solvent and/or C5-C10 paraffins solvent; after the acidification, further including the step of extracting with ester solvent.

8. The method according to claim 7, characterized in that: in the step (1), further including the step of adding an additive; the additive is at least one of a phase transfer catalyst, disodium ethylene diamine tetraacetate aqueous solution and the alkaline compound; the phase transfer catalyst is selected from any one of benzyl triethyl ammonium chloride, tetrabutyl ammonium bromide, tetrabutyl ammonium chloride, tetrabutyl ammonium iodide, tetrabutyl ammonium bisulfate, trioctylmethyl ammonium chloride, dodecyltrimethyl ammonium chloride and tetradecyl trimethyl ammonium chloride; the molar concentration of the disodium ethylene diamine tetraacetate aqueous solution is 0-0.001 mol/L, but is not 0.

9. The method according to claim 8, characterized in that: the medium in the reactions of step (1), step (2), step (3) and step (4) is selected from at least one of ether solvent, alcohol solvent, ester solvent, halogenated alkane solvent, C5-C10 paraffins solvent, amide solvent, nitrile solvent and water; the ether solvent is one of ether, dipropyl ether, dibutyl ether, methyl tertiary butyl ether, 1,3-dioxane, 1,4-dioxane, tetrahydrofuran, dimethoxymethane, ethylene glycol monomethyl ether, glycol dimethyl ether, ethylene glycol monomethyl ether, ethylene glycol diethyl ether and tert-butyl methyl-ether; the alcohol solvent is one of methanol, ethanol, normal propyl alcohol, isopropanol, normal butanol, sec-butyl alcohol, tert-butyl alcohol and glycol; the ester solvent is one of ethyl acetate, methyl acetate, propyl acetate, tert-butyl acetate and ethyl formate; the halogenated alkane solvent is one of methylene dichloride, trichloromethane and 1,2-methylene dichloride; the C5-C10 paraffins solvent is one of pentane, n-hexane, n-heptane, toluene and xylene; the amide solvent is one of N,N-dimethyl methanamide and N,N-dimethyl acetamide; the nitrile solvent is one of acetonitrile and propionitrile.

\* \* \* \* \*